United States Patent [19]

Sakakida et al.

[11] 4,177,108

[45] Dec. 4, 1979

[54] PROCESS FOR PRODUCING EMITANIN

[76] Inventors: Koji Sakakida, 26-11, 5-chome, Kamisaginomiya, Nakano-ku, Tokyo, Japan, 165; Tetsuro Ikekawa, 12-5, 1-chome, Sodegaura, Narashino-shi, Chiba-ken, Japan, 275

[21] Appl. No.: 881,744

[22] Filed: Feb. 27, 1978

[30] Foreign Application Priority Data

Mar. 2, 1977 [JP] Japan .................................. 52-021456
Jun. 17, 1977 [JP] Japan .................................. 52-071130

[51] Int. Cl.² .............................................. C12D 13/00
[52] U.S. Cl. ........................................ 435/74; 435/74; 435/171
[58] Field of Search ............................................. 195/81

[56] References Cited

FOREIGN PATENT DOCUMENTS 48-6766 2/1973 Japan .

OTHER PUBLICATIONS

Ikekawa et al., Cancer Research, vol. 29, pp. 734–735 (1969).
Yoshioka et al., Chem. Pharm. Bull., vol. 20, pp. 1175–1180 (1972); vol. 21, pp. 1772–1776 (1973).
Ikekawa et al., Cancer Chemotherapy Reports Part I, 57, pp. 85–86 (1973).
Yoshioka et al., Carbohydrate Research 43, pp. 305–320 (1975).

*Primary Examiner*—Lionel M. Shapiro
*Attorney, Agent, or Firm*—Oblon, Fisher, Spivak, McClelland & Maier

[57] ABSTRACT

EMITANIN having antitumor activity is produced by inoculating mycelia of *Tricholoma matsutake*, *Tricholoma baka-matsutake*, *Volvariella volvacea* or *Tremella fuciformis* in a medium for growing mycelia and fermenting the grown mycelia in a liquid medium containing a carbohydrate and a nitrogen source and isolating solid substance of mycelia from a broth and extracting the solid substance of mycelia and isolating the active ingredient.

19 Claims, No Drawings

PROCESS FOR PRODUCING EMITANIN

BACKGROUND OF THE INVENTION

1. Field of the Invention

The present invention relates to a process for producing EMITANIN having antitumor activity by a fermentation of mycelia of *Tricholoma matsutake, Tricholoma baka matsutake, Volvariella volvacea* or *Tremella fuciformis*.

2. Description of the Prior Art

The inventors have studied antitumor activity of the products prepared from edible mushrooms (Japanese Pat. No. 74450). The study was the first study on the antitumor activity of the products prepared from edible mushrooms.

SUMMARY OF THE INVENTION

It is an object of the present invention to provide a process for producing EMITANIN having antitumor activity.

It is another object of the present invention to provide a process for isolating EMITANIN having antitumor activity.

The foregoing and other objects of the present invention have been attained by inoculating mycelia of *Tricholoma matsutake, Tricholoma baka-matsutake, Volvariella volvacea* or *Tremella fuciformis* in a medium for growing mycelia and fermenting the grown mycelia in a liquid medium containing a carbohydrate and a nitrogen source and isolating solid substance of mycelia from a broth and extracting the solid substance of mycelia with hot water and isolating the active ingredients, EMITANIN-M-A,B and C; EMITANIN-BM-A,B and C; EMITANIN-F-A,B and C; and EMITANIN-S-A, B and C. In the isolation of the active ingredient from the extract or the broth filtrate, a lower alcohol or acetone is added to the extract or the broth filtrate and the precipitate is further purified.

DETAILED DESCRIPTION OF THE PREFERRED EMBODIMENTS

In the process of the present invention, mycelia of *Tricholoma matsutake, Tricholoma baka-matsutake, Volvariella volvacea* or *Tremelia fuciformis* are fermented in a liquid medium. It is preferable to grow seed mycelia on an agar plate by inoculating the mycelia and then, to homogenize the grown mycelia in the liquid medium containing a carbohydrate and a nitrogen source.

After the fermentation of the mycelia in the liquid medium, the mycelia are isolated from a broth by a filtration or a centrifugal separation. After the separation, the active ingredient in the mycelia is extracted with a hot water and is precipitated by adding a lower alcohol or acetone and is purified to obtain EMITANIN-A. The supernatant of the extract is concentrated to obtain EMITANIN-B.

On the other hand, the ingredient in the broth filtrate is precipitated by adding a lower alcohol or acetone and is purified to obtain EMITANIN-C. In the purification of the precipitate, the precipitate is dissolved in an aqueous solution and the impurities are separated by a centrifugal separation and the active ingredient in the solution is purified by an ion exchange resin treatment, a dialysis, a ultrafiltration with a molecular sieve membrane, a fractional precipitation with an organic solvent, an acid or a quaternary ammonium salt or a chromatographic separation and the active ingredient is dried.

The mycelia used in the present invention can be obtained from *Tricholoma matsutake* IFO 6915-6935 deposited in the Japanese Federation of Culture Collections of Micro-organisms, or *Volvariella volvacea* or *Tremella fuciformis* identified by "Coloured Illustrations of Fungi of Japan" written by Rokuya Imazeki and Tsuguo Hongo, published by Hoikusha and are deposited as FERM-P-4393 and FERM-P-4394 and *Tricholoma baka-matsutake* is deposited as FERM-P-4395 in the Japanese Fermentation Research Institute. *Tricholomo matsutake, Tricholoma baka-matsutake, Volvariella volvacea* or *Tremella fuciformis* is washed with a sterilized water and the surface is wiped with a cotton impregnating 70% ethanol to sterilize it and it is ground in small pieces by cutting, slicing, mincing or homogenizing it and it is inoculated on an agar plate under a sterilized condition.

The agar slant preferably contain a carbohydrate and an amino acid or a polypeptide for example, 2% of glucose and 0.2 to 0.5% of yeast extract and optionally, other additives (such as $KH_2PO_4$, $MgSO_4$, etc.). The mycelia are usually grown on the agar slant having pH of 4.0 to 7.5 at 20 to 70° C. for 1 to 5 weeks to easily obtain the mycelia which have high propagative activity in comparison with the stored mycelia. It is possible to add a contaminated-bacteria inhibitor or a growth-promoting substance for the mycelia to the agar slant. The mycelia can be also isolated by the well-known spora-print-isolation method.

The mycelia grown from the fruit body or from the agar slant of mycelia are inoculated in a liquid medium containing a carbohydrate such as hexose e.g. glucose or saccharose as a carbon source and an amino acid or a peptide such as amino acids, yeast extract and peptone ammonium salts as a nitrogen source and a small amount of inorganic or organic additives such as potassium phosphate, magnesium sulfate, ferric citrate, nicotinic acid derivatives, folic acid, thiamine derivatives, etc.

The nitrogen sources and the carbohydrate sources and the other additives for the medium are conventional sources disclosed in various prior arts, such as Biochemical Engineering (University of Tokyo Press).

Optimum nitrogen sources include ammonium tartrate or citrate, yeast extract, malt extract, corn steep liquor, distillers soluble peptone, amino acids, dried yeast, soybean meal, etc. Optimum carbohydrate sources include glucose, mannose, fructose, saccharose, maltose, dextrin, lactose, etc.

The fermentation is preferably carried out at 20° to 32° C. in the liquid medium having pH of 4.0 to 7.5 under stand-still or reciprocal or rotary shaking at 50 to 120 rpm for 2 to 50 days.

After the fermentation, the broth of the fermented product is treated by a solid-liquid separation such as filtration and a centrifugal separation to isolate the solid substance of mycelia. The active ingredients of EMITANIN-A and B are included in the solid substance of the mycelia separated by the filtration or the centrifugal separation etc. The active ingredient of EMITANIN-C is included in the filtrate of the broth.

The solid substance of mycelia is treated with suitable amount of a hot water at 80° to 100° C. for several hours to extract the active ingredient. A lower alcohol or acetone is added to the extract to precipitate the active ingredient and the active ingredient is separated by a centrifugal separation at 3,000 to 5,000 rpm for 15 minutes. The precipitate is dried by a lyophilization to obtain white gray powder of EMITANIN-A. The supernatant of the extract is condensed under a reduced pressure to distil off the lower alcohol or acetone and the concentrate is dried by a lyophilization to obtain white gray powder EMITANIN-B.

On the other hand, the broth filtrate obtained by separating the solid substance of mycelia from the broth, is treated by the fractional precipitation method adding 1 to 5 times of a lower alcohol or acetone to the filtrate and the precipitate is separated by a filtration or a centrifugal separation and is dried by a lyophilization to white gray powder of EMITANIN-C.

In the purification of the resulting precipitate or the separated powder, the precipitate or powder is dissolved in a hot water or a dilute alkaline aqueous solution and the insoluble impurities are separated by a filtration or a centrifugal separation. When the dilute alkaline aqueous solution is used, it is neutralized with an acid such as acetic acid and the active ingredient is isolated by a fractional precipitation by varying pH of the aqueous solution, and a treatment with an ion-exchange resin. For example, the impurities are separated by treating the precipitate with a weak ion-exchange resin of Duolite A-7 or Duolite S-30 or Amberlite IR-45. The solution is optionally treated by ultrafiltration with a molecular sieve membrane such as Diaflow membrane and the residue on the membrane is purified by a fractional precipitation with a water miscible organic solvent e.g. a lower alcohol or acetone; an acid such as acetic acid or a quaternary ammonium salt such as CPC, CTA, CTAB etc. The active ingredient can be further purified by an ion exchange gel chromatography using DEAE, ECTEOLA cellulose ion exchanger or Sephadex (e.g. DEAE Sephadex) etc. The active ingredient can be also purified by an affinity chromatography using a special adsorbent such as Concanavalin A-Sephrose. Then, the active ingredient is precipitated by adding a lower alcohol or acetone to the aqueous solution and the precipitate is isolated by a dialysis and dried by a lyophilization and other optional operation.

EMITANIN having antitumor activity obtained by the process of the present invention is considered to be a polysaccharide since it has the following characteristics.

Phenol sulfuric acid reaction...positive
Molisch reaction...positive
Anthrone sulfuric acid reaction...positive
Periodide benzidine reaction...positive
Naphthoresolcin reaction...positive
Iron perchlorate reaction...negative
Magnesium acetate reaction...negative.

The infrared spectral analyses support the consideration.

EMITANIN is soluble in water but insoluble in organic solvents such as benzene, hexane, acetone etc. and slightly soluble in a hot methanol or hot ethanol. The physico-chemical properties of EMITANIN are shown in Table 1.

Antitumor bioassy was performed by using the active ingredient obtained by the process of the present invention.

After 24 hours from subcutaneous transplantation of Sarcoma 180 ascites to ICR mice, the active ingredient of the present invention was interaperitoneally administrated for 10 days.

After 5 weeks from the inoculation, average solid tumor weight of the treated group was compared with that of the untreated group.

As the results, the inhibition percents of EMITANIN-M-A, B and C obtained from Tricholoma matsutake at a dose of 10 mg/kg/day were respectively 78%, 78% and 80%, $LD_{50}$ of EMITANIN-M-A, B and C were more than 2,000 mg/kg. (i.p.).

The inhibition percents of EMITANIN-BM-A, B and C obtained from Tricholoma baka matsutake at a dose of 10 mg/kg/day were respectively 84.6%, 68.5% and 75%. $LD_{50}$ of EMITANIN-BM-A, B and C were more than 2,000 mg/kg.(i.p.).

The inhibition percents of EMITANIN-F-A, B and C obtained from *Volvariella volvacea* at a dose of 30 mg/kg/day were respectively 72.5%, 75.1% and 75.5%. $LD_{50}$ of EMITANIN-F-A, B and C were more than 2,000 mg/kg (i.p.). The inhibition percents of EMITANIN-S-A, B and C obtained from Tremella fuciformis at a dose of 50 mg/kg/day were respectively 70%, 72.5% and 72%. $LD_{50}$ of EMITANIN-S-A, B and C were more than 2,000 mg/kg. (i.p.).

When EMITANIN-BM-B was orally administered at a dose of 300 mg/kg/day for 10 days, the inhibition percent was 50.68%.

The following is the physico-chemical properties of the active ingredients prepared by the process of the present invention. Each of EMITANIN decomposed at 150° to 260° C.

Table 1

|  | EMITANIN -M-A | EMITANIN -M-B | EMITANIN -M-C |
|---|---|---|---|
| Molecular weight | $>10^4$ | $<10^5$ | $<5 \times 10^4$ |
| Elementary analysis | C: 35.94 | C: 34.14 | C: 35.25 |
|  | H: 9.28 | H: 6.40 | H: 7.12 |
|  | N: 2.53 | N: 2.59 | N: 3.67 |
|  | O: 50.18 |  |  |
| Coloring reaction: |  |  |  |
| phenol sulfuric acid reaction | + | + | + |
| Molisch reaction | + | + | + |
| Anthrone sulfuric acid reaction | + | + | + |
| [α] | +23° | +22° | +20° |
| IR | O—H stretching vibration at region around 3300 cm$^{-1}$ | | |
|  | C—H stretching vibration at region around 2900 cm$^{-1}$ | | |
|  | C—H, C—O deformation vibration at region of 1,000–1,100 cm$^{-1}$ | | |
| UV | No characteristic absorption | | |
| Saccharide | glucose 30% | glucose >80% | glucose >50% |
|  | galactose 30% |  |  |
|  | mannose 35% |  |  |
| Saccharide content | >90% | >60% | >70% |
|  | EMITANIN -BM-A | EMITANIN -BM-B | EMITANIN -BM-C |
| Molecular weight | $>10^4$ | $<10^5$ | $<5 \times 10^4$ |
| Elementary analysis | C: 32.52 | C: 31.44 | C: 31.79 |
|  | H: 7.43 | H: 6.67 | H: 7.53 |
|  | N: 5.04 | N: 2.31 | N: 3.11 |
|  | O: 52.21 |  |  |
| Coloring reaction: |  |  |  |
| phenol sulfuric acid reaction | + | + | + |
| Molisch reaction | + | + | + |
| Anthrone sulfuric acid reaction | + | + | + |
| [α] | +25° | +19° | +10° |
| IR | O—H stretching vibration at region around 3300 cm$^{-1}$ | | |
|  | C—H stretching vibration at region around | | |

Table 1-continued

| | | | |
|---|---|---|---|
| | 2900 cm$^{-1}$ C—H, C—O deformation vibration at region of 1,000-1,100 cm$^{-1}$ | | |
| UV | No characteristic abosrption | | |
| Saccharide | glucose 30% galactose 30% mannose 30% | glucose >80% | glucose >50% |
| Saccharide content | >90% | >50% | >60% |
| | EMITANIN-F-A | EMITANIN-F-B | EMITANIN-F-C |
| Molecular weight | >10$^4$ | <10$^5$ | <5 × 10$^4$ |
| Elementary analysis | C: 36.42 H: 6.05 N: 8.88 O: 45.54 | C: 42.86 H: 7.11 N: 10.87 | C: 40.35 H: 7.56 N: 10.55 |
| Coloring reaction: | | | |
| phenol sulfuric acid reaction | + | + | + |
| Molisch reaction | + | + | + |
| Anthrone sulfuric acid reaction | + | + | + |
| [α] | +13° | −21° | −10° |
| IR | O—H stretching vibration at region around 3300 cm$^{-1}$ C—H stretching vibration at region around 2900 cm$^{-1}$ C—H, C—O deformation vibration at region of 1,000-1,100 cm$^{-1}$ | | |
| UV | No characteristic absorption | | |
| Saccharide | glucose >90% | glucose >90% | glucose >60% |
| Saccharide content | >30% | >30% | >25% |
| | EMITANIN-S-A | EMITANIN-S-B | EMITANIN-S-C |
| Molecular weight | >10$^4$ | <10$^5$ | <5 × 10$^4$ |
| Elementary analysis | C: 36.68 H: 5.71 N: 3.46 O: 53.15 | C: 35.08 H: 5.49 N: 5.30 | C: 32.12 H: 6.38 N: 6.89 |
| Coloring reaction: | | | |
| phenol sulfuric acid reaction | + | + | + |
| Molisch reaction | + | + | + |
| Anthrone sulfuric acid reaction | + | + | + |
| [α] | −20° | +3° | −5° |
| IR | O—H stretching vibration at region around 3300 cm$^{-1}$ C—H stretching vibration at region around 2900 cm$^{-1}$ C—H, C—O deformation vibration at region of 1,000-1,100 cm$^{-1}$ | | |
| UV | No characteristic absorption | | |
| Saccharide | galactose 50% mannose 40% | glucose >30% | glucose >30% |
| Saccharide content | >55% | >10% | >10% |

The present invention will be further illustrated by certain examples.

EXAMPLE 1

The stored mycelia of (*Tricholoma matsutake* (S. Ito et Imai) Sing.) IFO 6915 was inoculated on an agar slant containing 2% of glucose and 0.5% of yeast extract (pH 4.5) and fermented at 22° C. for 3 weeks. Then, the mycelia grown on the agar plate were isolated and carefully homogenized and inoculated into 3 liters of a liquid medium containing 2% of glucose and 0.5% of dried yeast (pH 4.5) and they were fermented at 24° C. for 5 weeks with gradually shaking the liquid medium. After the fermentation, mycelia and broth filtrate were separated by a centrifugal separation. The mycelia were extracted twice, with 1 liter of a boiling water for 5 hours and the extract was condensed to about 1 liter under a reduced pressure. After cooling the condensed extract, 3 volumes of ethanol was added to 1 volume of the condensed extract. The precipitate was separated by a fractional precipitation with a centrifugal separation. The precipitate thus obtained was dissolved in 100 ml. of water and 30 ml. of 0.5 N-NH$_4$OH was added. The resulting precipitate was separated by a centrifugal separation and further separated by a dialysis and a lyophilization to obtain 124 mg. of a white powder of EMITANIN-M-A.

On the other hand, the supernatant was heated under a reduced pressure to evaporate ethanol and to obtain 193 mg. of a white powder of EMITANIN-M-B.

On the other hand, 3 volumes of ethanol was added to 1 volume of the broth filtrate of the fermentation and the precipitate was separated in accordance with the above-mentioned procedure. The active ingredient was further purified with Sephadex G-200 column chromatography by eluting with deionized water to obtain 63 mg of a white powder of EMITANIN-M-C.

EXAMPLE 2

The mycelia of *Volvariella volvacea* (Fr.)Sing.- (FERM-P-4393) were inoculated in a liquid medium containing 1% of glucose, 0.4% of malt extract and 0.15% of yeast extract at pH of 6.5 and it was fermented at 30° C. for 3 days and further fermented at 270° C. for 3 days with a reciprocal shaking at 120 rpm.

The fermentation product of 3 liters of the medium was treated by a centrifugal separation at 5,000 rpm for 10 minutes to obtain 26.4 g of mycelia (wet weight). The mycelia were extracted with 2 liters of water at 100° C. for 3.5 hours. The extract was condensed under a reduced pressure and treated by a lyophilization to obtain 1.463 g of powder.

In 100 ml of water 1 g of the powder was dissolved and 400 ml. of ethanol was added to the solution and the precipitate was separated by a centrifugal separation at 5,000 rpm for 15 minutes and then treated by a lyophilization to obtain 94 mg of EMITANIN-F-A.

The supernatant was treated by a condensation under a reduced pressure and a lypophilization to obtain 836 mg of EMITANIN-F-B.

On the other hand, 3 volumes of ethanol was added to 1 volume of the broth filtrate and the precipitate was treated in accordance with the above-mentioned procedure to obtain 1055 mg of powder of EMITANIN-F-C.

EXAMPLE 3

In accordance with the process of Example 2, the mycelia of *Tremella fuciformis* Berk.(FERM-P-4394) were inoculated and fermented and separated to obtain 333 g of the mycelia (wet weight) from 3 liters of the fermentation solution. The mycelia were extracted with a boiling water and precipitated and dried to obtain 4.4 g of the powder. The powder was further treated in accordance with the process of Example 2 to obtain 82 mg of EMITANIN-S-A, and 851 mg of EMITANIN-S-B from 1 g of the powder.

On the other hand, the broth filtrate was treated in accordance with the above-mentioned process to obtain 985 mg of powder of the EMITANIN-S-C.

EXAMPLE 4

The stored mycelia of *Tricholoma baka-matsutake*(- FERM-P-4395) was inoculated on an agar slant containing 2% of glucose and 0.5% of yeast extract (pH 4.5) and fermented at 26° C. for 15 days. Then, the mycelia grown on the agar plate were isolated and carefully homogenized and inoculated into 3 liters of a liquid medium containing 2% of glucose and 0.5% of dried yeast (pH 4.5) and they were fermented at 24° C. for 3 weeks with gradually shaking the liquid medium. After the fermentation, mycelia and broth filtrate were separated by a centrifugal separation. The mycelia were extracted twice, with 1 liter of a boiling water for 5 hours and the extract was condensed to about 1 liter under a reduced pressure. After cooling the condensed extract, 3 volumes of ethanol was added to 1 volume of the condensed extract. The precipitate was separated by a fractional precipitation with a centrifugal separation. The precipitate thus obtained was dissolved in 100 ml. of water and 30 ml. of 0.5 N-NH$_4$OH was added. The resulting precipitate was separated by a centrifugal separation and further separated by a dialysis and a lyophilization to obtain 1.7 g of a white powder of EMITANIN-BM-A.

On the other hand, the supernatant was heated under a reduced pressure to evaporate ethanol and to obtain 5.7 g of a white powder of EMITANIN-BM-B.

On the other hand, 3 volumes of ethanol was added to 1 volume of the broth filtrate of the fermentation and the precipitate was separated in accordance with the above-mentioned procedure. The active ingredient was further purified with Sephadex G-200 column chromatography by eluting with deionized water to obtain 1.3 g of a white powder of EMITANIN-BM-C.

What is claimed is:

1. A process for producing EMITANIN which comprises inoculating mycelia of *Tricholoma matsutake, Tricholoma baka-matsutake, Volvariella volvaea* or *Tremella fuciformis* in a medium for growing mycelia and fermenting the grown mycelia in a liquid medium containing a carbohydrate and a nitrogen source and isolating solid substance of mycelia from a broth and extracting the solid substance of mycelia with a hot water and isolating the active ingredients.

2. A process according to claim 1 wherein a precipitating agent of a lower alcohol, acetone, an acid or a quaternary ammonium salt is added to the extract obtained by extracting the mycelia separated from the broth and the precipitate is purified to obtain EMITANIN-A.

3. A process according to claim 2 wherein the precipitate is dissolved in water or an aqueous solution and the solution is purified by a dialysis, an ultrafiltration, a fractional precipitation or a chromatographic separation.

4. A process according to claim 1 wherein the separation of mycelia is carried out by a centrifugal separation.

5. A process according to claim 2 wherein the separation of the precipitate is carried out by a centrifugal separation.

6. A process according to claim 2 wherein the extract is treated with the precipitating agent and the resulting precipitate is separated and the filtrate is purified to obtain EMITANIN-B.

7. A process according to claim 1 wherein a precipitating agent of a lower alcohol, acetone, an acid or a quaternary ammonium salt is added to a solution obtained by separating the mycelia from the broth, and the resulting precipitate is dissolved in water or an aqueous solution and the resulting solution is purified to obtain EMITANIN-C.

8. A process according to claim 1 wherein EMITANIN-M-A is isolated from a precipitate of the extract obtained by extracting the mycelia grown from the mycelia of *Tricholoma matsutake.*

9. A process according to claim 1 wherein EMITANIN-M-B is isolated from a supernatant of the extract obtained by extracting the mycelia grown from the mycelia of *Tricholoma matsutake.*

10. A process according to claim 1 wherein EMITANIN-M-C is isolated from a broth filtrate obtained by culturing and filtering the mycelia of *Tricholoma matsutake.*

11. A process according to claim 1 wherein EMITANIN-F-A is isolated from a precipitate of the extract obtained by extracting the mycelia grown from the mycelia of *Volvariella volvacea*(Fr) Sing.

12. A process according to claim 1 wherein EMITANIN-F-B is isolated from supernatant of the extract obtained by extracting the mycelia grown from the mycelia of *Volvariella volvacea*(Fr) Sing.

13. A process according to claim 1 wherein EMITANIN-F-C is isolated from a broth filtrate obtained by culturing and filtering the mycelia of *Volvariella volvacea*(Fr) Sing.

14. A process according to claim 1 wherein EMITANIN-S-A is isolated from a precipitate of the extract obtained by extracting the mycelia grown from the mycelia of *Tremella-funciformis* Berk.

15. A process according to claim 1 wherein EMITANIN-S-B is isolated from a supernatant of the extract obtained by extracting the mycelia grown from the mycelia of *Tremella-fuciformis* Berk.

16. A process according to claim 1 wherein EMITANIN-S-C is isolated from a broth filtrate obtained by culturing and filtering the mycelia of *Tremella-fuciformis* Berk.

17. A process according to claim 1 wherein EMITANIN-BM-A is isolated from a precipitate of the extract obtained by extracting the mycelia grown from the mycelia of *Tricholoma baka-matsutake.*

18. A process according to claim 1 wherein EMITANIN-BM-B is isolated from a supernatant of the extract obtained by extracting the mycelia grown from the mycelia of *Tricholoma baka-matsutake.*

19. A process according to claim 1 wherein EMITANIN-BM-C is isolated from a broth filtrate obtained by culturing and filtering the mycelia of *Tricholoma baka-matsutake.*

* * * * *